(12) United States Patent
Ramel

(10) Patent No.: US 7,771,655 B2  
(45) Date of Patent: Aug. 10, 2010

(54) MECHANICAL DEVICE FOR MIXING A FLUID SAMPLE WITH A TREATMENT SOLUTION

(75) Inventor: Urs A. Ramel, Sunnyvale, CA (US)

(73) Assignee: Bayer HealthCare LLC, Tarrytown, NY (US)

( * ) Notice: Subject to any disclaimer, the term of this patent is extended or adjusted under 35 U.S.C. 154(b) by 978 days.

(21) Appl. No.: 11/485,743

(22) Filed: Jul. 12, 2006

(65) Prior Publication Data

US 2008/0081378 A1 Apr. 3, 2008

(51) Int. Cl.
*G01N 21/01* (2006.01)

(52) U.S. Cl. .................. 422/63; 422/68.1; 422/100; 436/174; 206/222

(58) Field of Classification Search ............ 422/63, 422/68.1, 100; 436/174; 206/222
See application file for complete search history.

(56) References Cited

U.S. PATENT DOCUMENTS

| | | | |
|---|---|---|---|
| 4,024,857 A | 5/1977 | Blecher et al. | |
| 4,713,974 A | 12/1987 | Stone | |
| 4,935,010 A | 6/1990 | Cox et al. | |
| 5,061,632 A | 10/1991 | Shepherd et al. | |
| 5,208,163 A | 5/1993 | Charlton et al. | |
| 5,580,794 A | 12/1996 | Allen | |
| 5,837,546 A | 11/1998 | Langille et al. | |
| 5,885,527 A | 3/1999 | Buechler | |
| 5,912,134 A | 6/1999 | Shartle | |
| 5,945,345 A | 8/1999 | Blatt et al. | |
| 6,084,660 A | 7/2000 | Shartle | |
| 6,284,548 B1 | 9/2001 | Berndtsson | |
| 6,296,020 B1 | 10/2001 | McNeely et al. | |
| 6,426,230 B1 | 7/2002 | Feistel | |
| 6,521,182 B1 | 2/2003 | Shartle et al. | |
| 6,540,675 B2 | 4/2003 | Aceti et al. | |
| 6,652,814 B1 | 11/2003 | House et al. | |
| 6,673,627 B2 | 1/2004 | Tyrrell et al. | |
| 6,755,949 B1 | 6/2004 | Bhullar et al. | |
| 6,766,817 B2 | 7/2004 | da Silva et al. | |
| 6,767,510 B1 | 7/2004 | Buechler | |
| 6,830,936 B2 | 12/2004 | Anderson et al. | |
| 6,901,963 B2 | 6/2005 | Kim et al. | |
| 6,905,882 B2 | 6/2005 | Buechler | |
| 6,908,593 B1 | 6/2005 | Shartle | |
| 6,918,404 B2 | 7/2005 | Dias da Silva et al. | |

(Continued)

FOREIGN PATENT DOCUMENTS

EP 1486766 A1 12/2004

(Continued)

*Primary Examiner*—Jill Warden
*Assistant Examiner*—Timothy G Kingan
(74) *Attorney, Agent, or Firm*—Lerner, David, Littenberg, Krumholz & Mentlik, LLP

(57) ABSTRACT

A device for preparing a fluid sample for use in a fluid analyte meter, including: a first portion, comprising: a septum piercing projection, a capillary channel, and a vent on an outer surface of the first portion; and a second portion, comprising: a treatment solution chamber, and a septum sealing the treatment solution chamber, wherein the vent is open when the first portion of the device is initially inserted into the second portion of the device, and wherein the vent is closed when the first portion of the device is fully inserted into the second portion of the device.

14 Claims, 11 Drawing Sheets

U.S. PATENT DOCUMENTS

| | | |
|---|---|---|
| 6,919,046 B2 | 7/2005 | O'Connor et al. |
| 6,935,772 B2 | 8/2005 | Karp et al. |
| 6,959,615 B2 | 11/2005 | Gamble |
| 7,066,586 B2 | 6/2006 | da Silva et al. |
| 2004/0042930 A1 | 3/2004 | Clemens et al. |
| 2004/0063217 A1 | 4/2004 | Webster et al. |
| 2004/0069076 A1 | 4/2004 | Gamble |
| 2004/0168728 A1 | 9/2004 | Schober et al. |
| 2005/0014273 A1 | 1/2005 | Dahm et al. |
| 2005/0196872 A1 | 9/2005 | Nguyen et al. |
| 2006/0039833 A1 | 2/2006 | Yong |

FOREIGN PATENT DOCUMENTS

| | | |
|---|---|---|
| WO | WO 03/044488 A1 | 5/2003 |

MECHANICAL DEVICE FOR MIXING A FLUID SAMPLE WITH A TREATMENT SOLUTION

TECHNICAL FIELD

The present invention relates to mechanical devices for mixing a fluid sample (which may optionally be a blood sample) with a treatment solution (which may optionally be a buffer or diluent).

BACKGROUND OF THE INVENTION

Published U.S. Patent Application 2005/0196872, Ser. No. 11/043,510, entitled "Mechanical Device For Mixing A Fluid Sample With A Treatment Solution" describes a two part device for mixing a blood sample with a treatment solution prior to release of the treated sample into a fluid analyte meter. A disadvantage of this system is that it is difficult to control pressurization in the device such that a correct sample volume is delivered to the test cartridge. As will be shown, the present invention overcomes this disadvantage.

SUMMARY OF THE INVENTION

The present invention provides an integrated system for mixing a fluid sample with a treatment solution and for delivering the mixed fluid sample and treatment solution into a meter. In preferred aspects, the fluid sample is a blood sample, the treatment solution is a buffer and the meter is a blood analyte meter, however, the present invention is not so limited. In alternate aspects, the fluid sample may be a body fluid sample including interstitial fluid or a fluid sample containing a prostate specific antigen. Moreover, although the blood analyte meter may optionally include a hemoglobin A1c (HbA1c) or lipid panel meter, the present invention is again not so limited.

In one aspect, the present invention provides a device for preparing a fluid sample for use in a fluid analyte meter, comprising: a first portion, comprising: a septum piercing projection, a capillary channel, and a vent on an outer surface of the first portion; and a second portion, comprising: a treatment solution chamber, and a septum sealing the treatment solution chamber, wherein the vent is open when the first portion of the device is initially inserted into the second portion of the device, and wherein the vent is closed when the first portion of the device is fully inserted into the second portion of the device.

In accordance with the present invention, the vent permits air to escape from within the second portion of the device as the first portion of the device is inserted into the second portion of the device. The vent may comprise a slot extending along a portion of the outer surface of the first portion of the device. Optionally, the slot may extend from a leading edge of the outer surface part way along the length of the outer surface of the first portion of the device.

In another aspect, the present invention provides a device for preparing a fluid sample for use in a fluid analyte meter, comprising: a first portion having a capillary channel dimensioned to receive a fluid sample therein, and having a vent on an outer surface; a second portion having a treatment solution chamber enclosed by first and second septums, wherein the first portion penetrates the first septum when the first portion is inserted into the second portion such that contents of the treatment solution chamber mix with contents of the capillary channel, wherein the vent is open when the first portion of the device is initially inserted into the second portion of the device, and wherein the vent is closed when the first portion of the device is fully inserted into the second portion of the device; and a mechanism for penetrating the second septum such that contents of the treatment solution chamber and the capillary channel can be ejected from the device.

In yet another aspect, the present invention provides a device for preparing a fluid sample for use in a fluid analyte meter, comprising: a first portion having a capillary channel dimensioned to receive a fluid sample therein; a second portion having a treatment solution chamber enclosed by first and second septums, wherein the first portion penetrates the first septum when the first portion is inserted into the second portion such that contents of the treatment solution chamber mix with contents of the capillary channel; and a plunger having a mechanism for penetrating the second septum such that the contents of the treatment solution chamber and the capillary channel are ejected through the plunger. In preferred aspects, the mechanism for penetrating the second septum may comprise a spike on the plunger. Furthermore, the plunger may comprise a central flow channel, and wherein the spike is positioned adjacent to the central flow channel. A sharp end of the spike may be positioned over the central flow channel.

DETAILED DESCRIPTION OF THE DRAWINGS

Figures 1A, 1B, 1C:
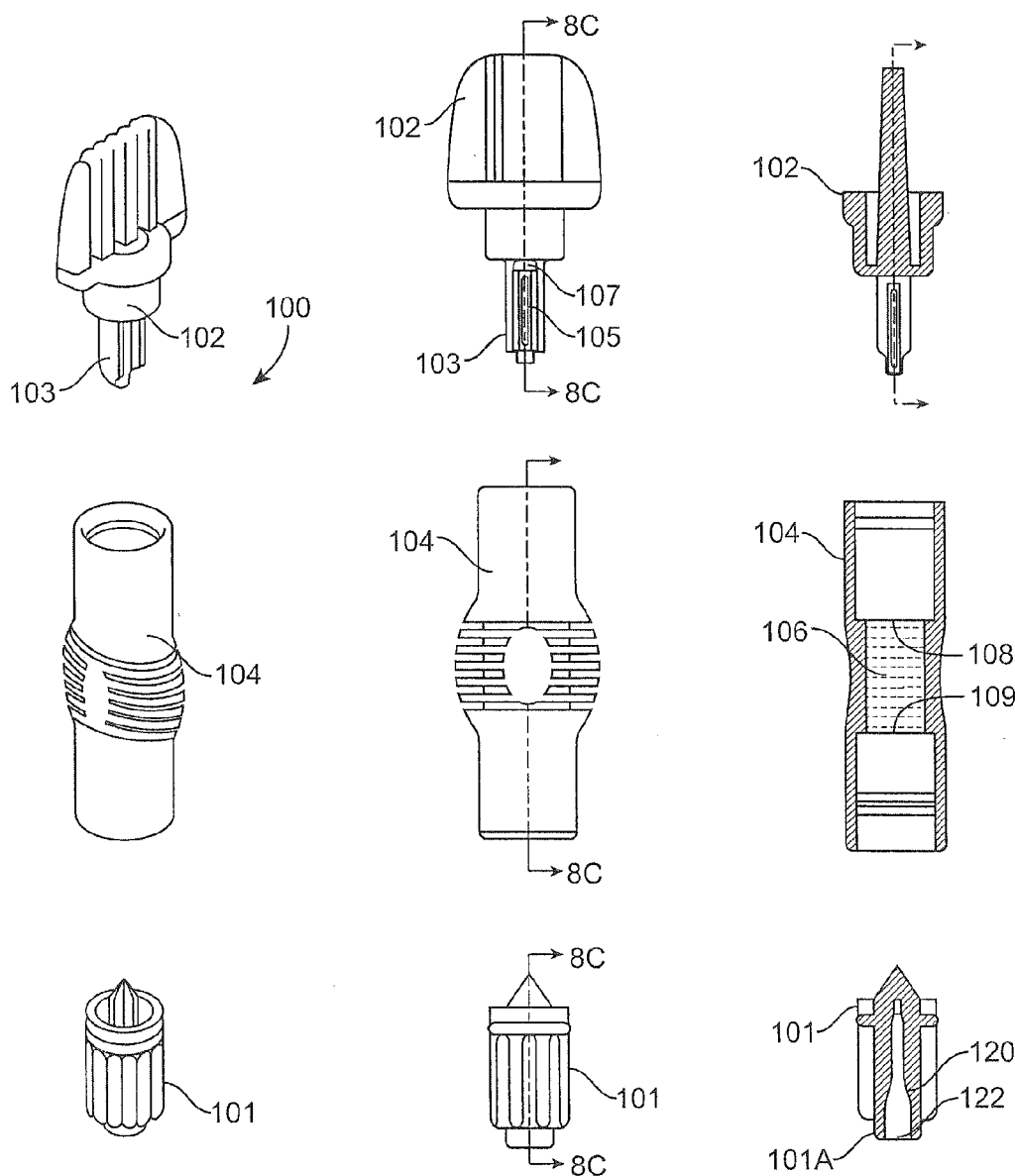
FIG. 1A is a perspective view of a prior art embodiment of the invention, as seen in Published U.S. Patent Application 2005/0196872, Ser. No. 11/043,510, entitled "Mechanical Device For Mixing A Fluid Sample With A Treatment Solution".
FIG. 1B is a side elevation view of the device of FIG. 1A.
FIG. 1C is sectional side elevation view corresponding to FIG. 1B.

FIGS. 1A to 1H show a prior art device as was described in FIGS. 8A to 8H of Published U.S. Patent Application 2005/0196872, Ser. No. 11/043,510, entitled "Mechanical Device For Mixing A Fluid Sample With A Treatment Solution", as follows.

Device 100 includes a first portion 102 having a septum piercing portion 103 with a capillary channel 105 therein; and a second portion 104, including a treatment solution chamber 106, and a top septum 108 sealing treatment solution chamber 106.

In one preferred method of operation, a user places a drop of blood from their finger at the top end of capillary channel 105. A stop junction 107 is provided at the opposite end of capillary channel 105. Such a stop junction may preferably comprise a bore passing through first portion 102 of device 100. Stop junction 107 thereby facilitates a predetermined volume of blood being received, into capillary channel 105.

Figure 1D:
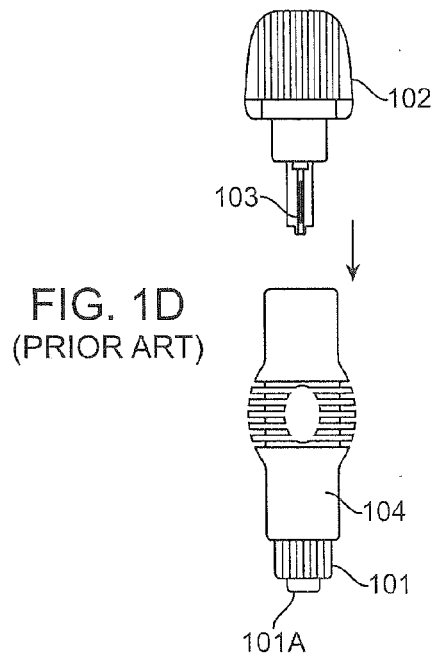
FIG. 1D is a side elevation view of the first portion of the device being inserted into the second portion of the device.
Figure 1E:
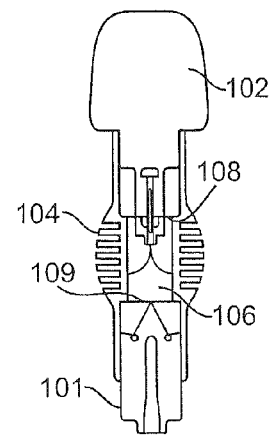
FIG. 1E is a sectional side elevation view corresponding to FIG. 1D.

As seen in FIGS. 1D and 1E, after capillary channel 105 has been filled with a blood sample, first portion 102 is then inserted into second portion 104 such that septum piercing projection 103 pierces through top septum 108, such that capillary channel 105 is received into treatment solution chamber 106. Thus, the contents of capillary channel 105 and treatment solution chamber 106 mix together. Mixing may be further enhanced by shaking the device.

Figure 1F:
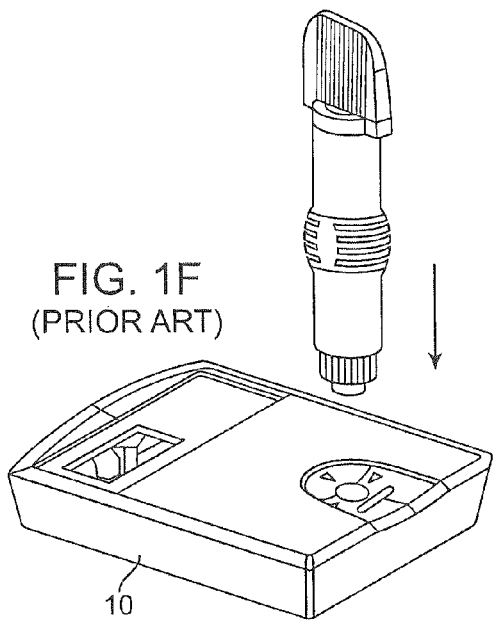
FIG. 1F is a perspective view of the device being inserted into a meter.
Figure 1G:
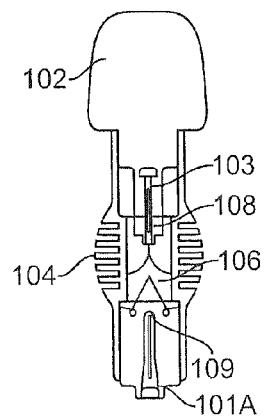
FIG. 1G is a sectional side elevation view corresponding to FIG. 1F.

Lastly, as seen in FIGS. 1F and 1G, dispensing nozzle 101 can be moved with respect to first portion 102 such that a second (i.e.: bottom) septum 109 is penetrated by first portion 102. When this occurs, the mixed blood/treatment solution is ejected from the device through dispensing nozzle 101. In preferred embodiments, distal end 101A of dispensing nozzle 101 is dimensioned to be received into a port of a blood analyte meter 10 (that may optionally comprise a hemoglobin A1c blood meter). This device may be used with any suitable fluid analysis meter, or even with a simple containment vessel (e.g.: for preparing a sample for deposition in a well, such that it can be analyzed in future).

Referring back to FIG. 1C, optional internal features of dispensing nozzle 101 are illustrated. For example, (in contrast to FIG. 1C), the internal channel 120 through which fluid is ejected can be flared. This has the advantage of slowing the flow of solution into meter 10, which prevents splashing inside meter 10. In addition, an air vent 120 can also be provided to air pressure buildup during operation.

Dispensing nozzle 101 is received into first portion 104, as illustrated. This has the advantage of trapping the blood/treatment solution mixture such that it can all be ejected through dispensing nozzle 101.

First and second septums 108 and 109 may be made of foil or any suitable material, including plastic or rubber.

System 100 may also be used for preparing a blood sample for use in a blood analyte meter 10 by: drawing blood into capillary channel 105 in a body 102 having a septum piercing projection 103; piercing a first septum 108 covering treatment solution chamber 106 with septum piercing projection 103, thereby exposing the blood in capillary channel 105 to the contents of treatment solution chamber 106; shaking treatment solution chamber 106 with capillary channel 105 received therein, thereby mixing the blood with the contents of treatment solution chamber 106; and piercing a second septum 109 such that the mixed blood and treatment solution chamber contents are received into blood analyte meter 10.

System 100 may also be used for preparing a blood sample for use in blood analyte meter 10, by: drawing a blood sample into capillary channel 105 in first portion 102 of the device; moving a first portion 102 of the device with respect to second portion 104 to penetrate septum 108 of treatment solution chamber 106 such that contents of treatment solution chamber 106 are mixed with the blood sample in capillary channel 105; and ejecting the mixed treatment solution and blood sample through dispensing nozzle 106 and into a blood analyte meter 10.

Figure 1H:
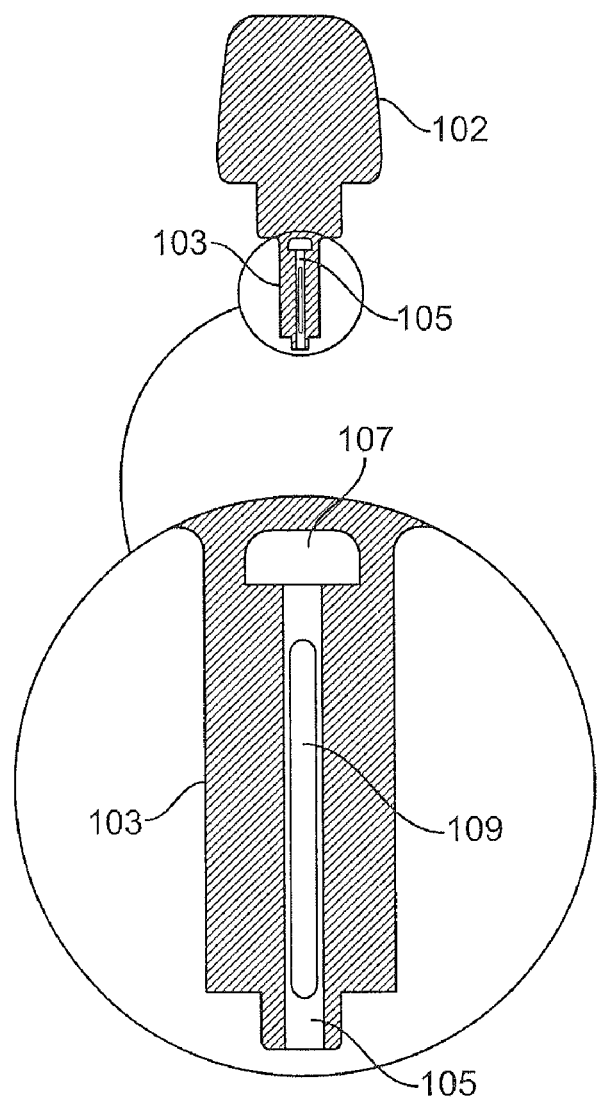
FIG. 1H is an illustration of a system for easier washout in the first portion of the device.

FIG. 1H illustrates a system for easier washout of capillary channel 105 in septum piercing projection 103 of first portion 102, as follows. An open window 109 is provided in the side of capillary channel 105 to permit easier washout of the fluid sample, for better mixing.

FIGS. 2A to 2D show an embodiment of the present invention having a vent in the first portion of the device. This vent ensures that first portion 202 is inserted into second portion 204 at the same time regardless of the user technique or the parts themselves. An advantage of this controlled pressurization is that it ensures a correct volume delivery to a test cartridge that may be used with the device. Specifically, an exact pre-measured dose of the treated sample fluid can be squirted out of the device when the second septum in the second portion of the device is ruptured, as follows.

The embodiment of the invention presented in FIGS. 2A to 3D operates similar to the above described embodiment of the invention set forth in FIGS. 1A to 1H, but has further novel features, including but not limited to, the following.

Device 200 (FIG. 2A) includes a first portion 202 having a septum piercing projection 203 with a capillary channel 205 therein; and a second portion 204 including a treatment solution chamber 206 with a top septum 208 sealing treatment solution chamber 206. Similar to the prior art device set forth in FIGS. 1A to 1H, a user places a drop of blood in capillary channel 205. A stop junction 207 operates similar to stop junction 205. After capillary channel 205 has been filled with blood, first portion 202 is then inserted into second portion 204. Septum piercing projection 203 will then rupture 208 such that capillary channel 205 will be received within treatment solution chamber 206 (in second portion 204).

As shown in FIGS. 2A to 2D, a vent 220 is provided in an outer surface 222 of first portion 202. Vent 22 may simply comprise a slot cut out of first portion 202. Preferably, vent 220 extends from a leading edge 224 of outer surface 222 of first portion 202 of device 200.

Figure 2A:
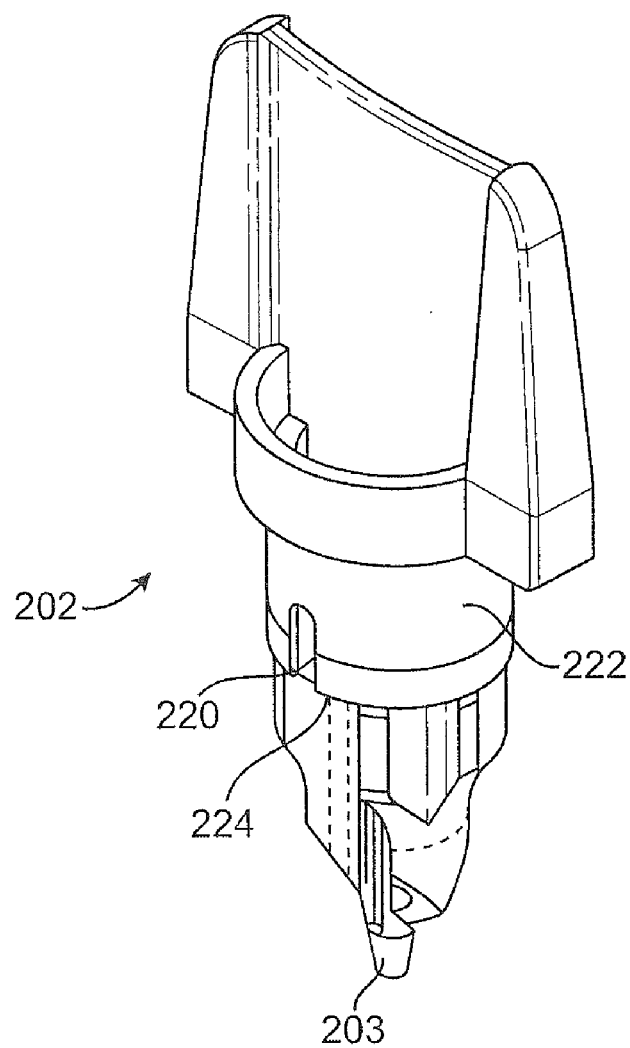
FIG. 2A is a perspective view of an embodiment of the present invention showing the first portion of the device having a vent slot therein.
Figure 2B:
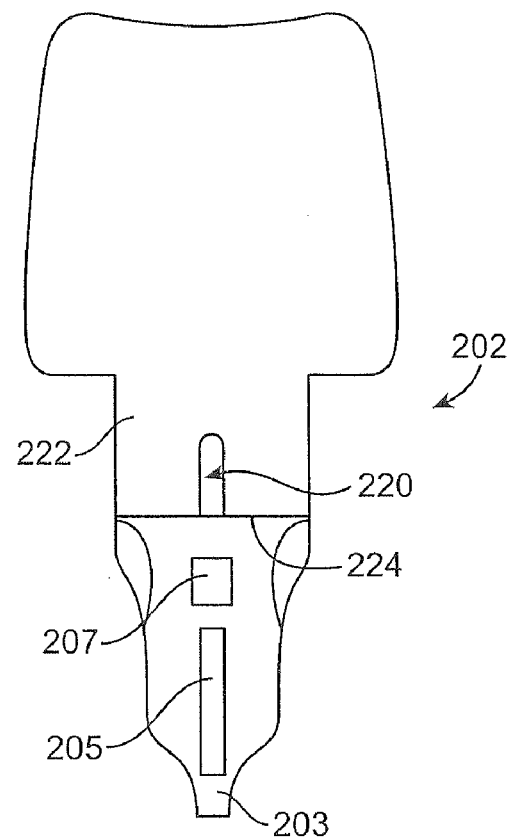
FIG. 2B is a side elevation view corresponding to FIG. 2A prior to the insertion of the first portion of the device into the second portion of the device.
Figure 2B:
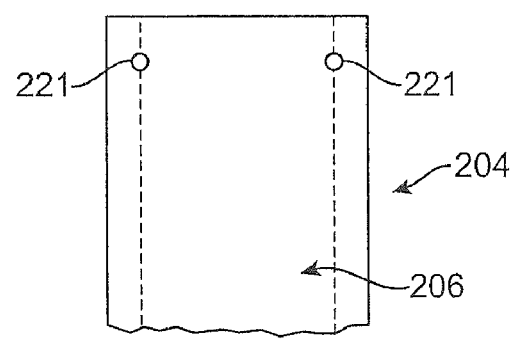
Figure 2C:
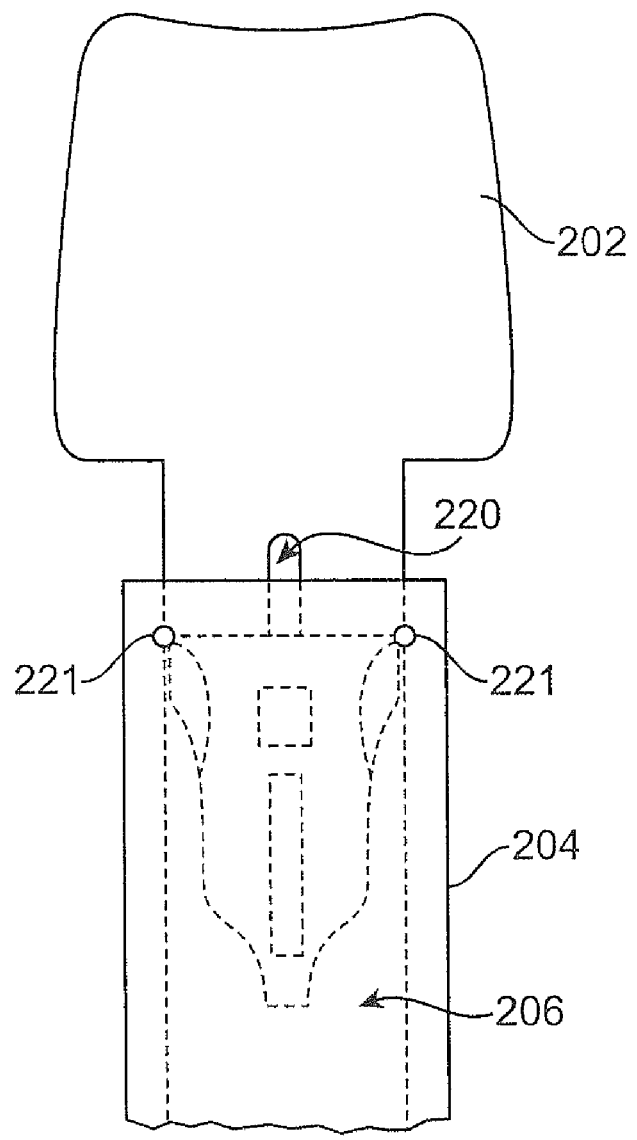
FIG. 2C is a side elevation view corresponding to FIG. 2A showing partial insertion of the first portion of the device into the second portion of the device.
Figure 2D:
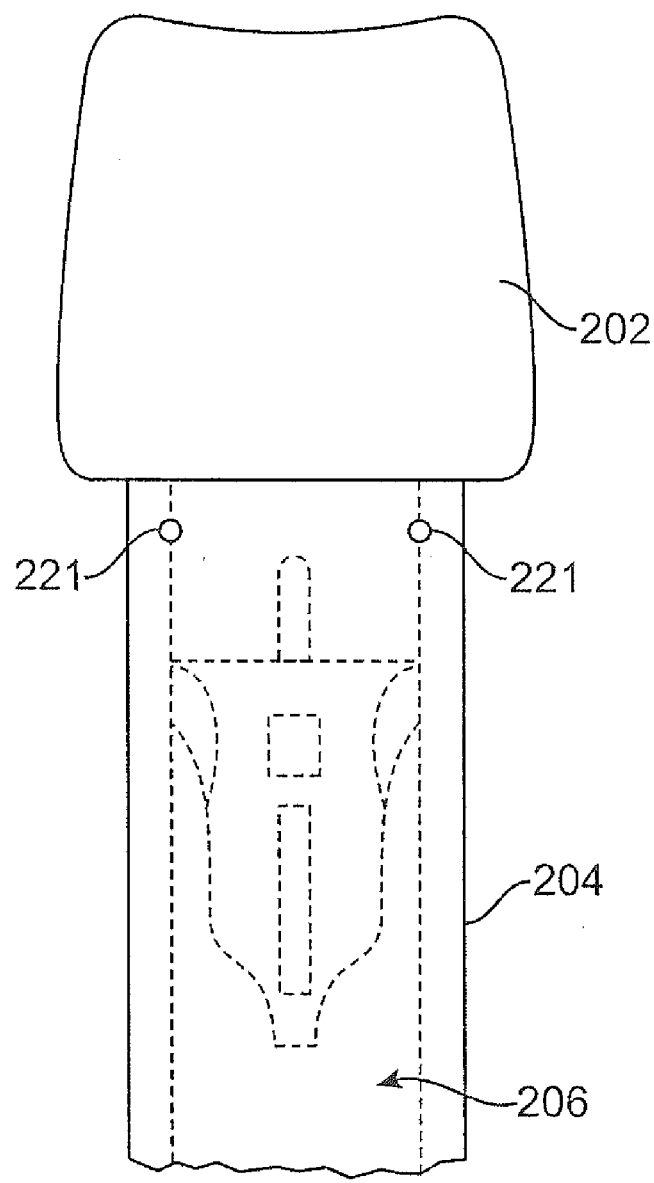
FIG. 2D is a side elevation view corresponding to FIG. 2A showing full insertion of the first portion of the device into the second portion of the device.

As seen viewing FIGS. 2B to 2D, vent 220 permits air to escape from within second portion 204 as first portion 202 is inserted into second portion 204 of the device. FIG. 2B shows first portion 202 prior to insertion into second portion 204. FIG. 2C shows first portion 202 partially inserted into second portion 204. As can be seen, vent 220 permits air to escape from chamber 206 as first portion 202 is inserted into second portion 204. Lastly, as seen in FIG. 2D, first portion 202 is fully inserted into second portion 204. Therefore, the contents of capillary channel 205 and solution treatment chamber 206 can be mixed without any of the fluid dripping out of vent 220. At this time, no further air can escape from chamber 206 through vent 220 (since vent 220 is fully received within second portion 204).

As can be seen, outer surface 220 of first portion 202 is positioned against an inner surface of second portion 204. In the exemplary embodiment shown, vent 220 becomes fully sealed when it passes seal ring 221 in second portion 204. Typically, first portion 202 will travel about 0.001" past the sealing point until it is fully inserted into second portion 204. The movement (of first portion 202 into second portion 204) along this additional small travel distance pressurizes the chamber. This ensures a correct volume delivery to a test cartridge that may be used with the device. Specifically, an exact pre-measured dose of the treated sample fluid can be squirted out of device 200 when second septum 209 (FIGS. 2B and 2C) in second portion 204 of device 200 is ruptured. Therefore, an advantage of vent 220 is that its presence ensures that first portion 202 is inserted into second portion 204 at the same time regardless of the user technique or the parts themselves.

FIGS. 2A to 2C show operation of device 200, as follows. First portion 202 and second portion 204 operate similar to respective first and second portions 102 and 104 as seen in the prior art device of FIGS. 1A to 1H. A plunger 201 is provided. Plunger 201 operates the same as dispensing nozzle 101 as described above. A bottom cap is also provided.

Figure 3A:
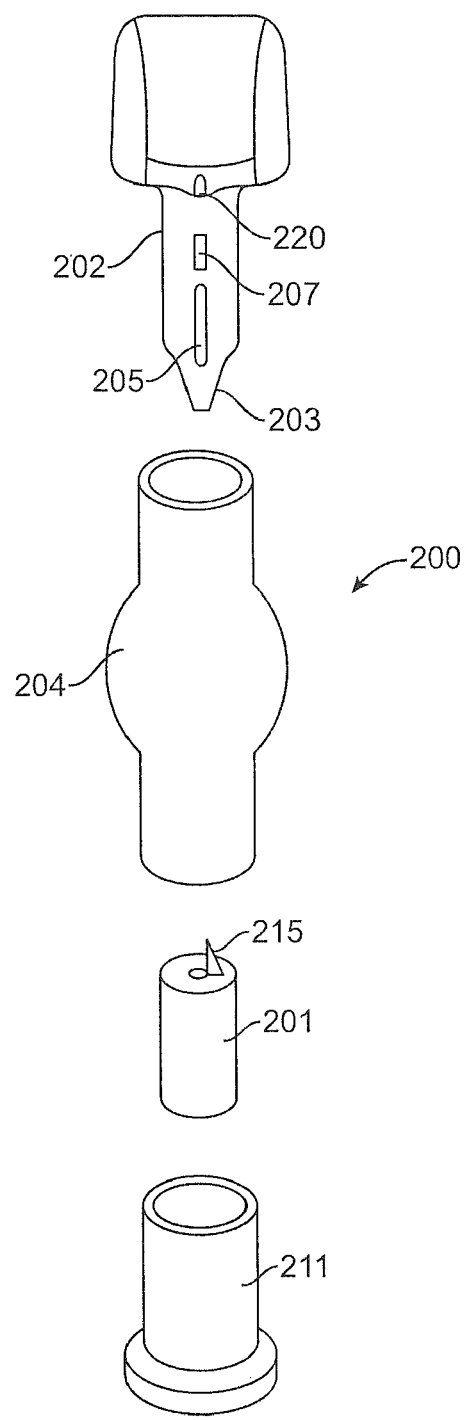
FIG. 3A is an exploded view of another embodiment of the present invention.
Figure 3B:
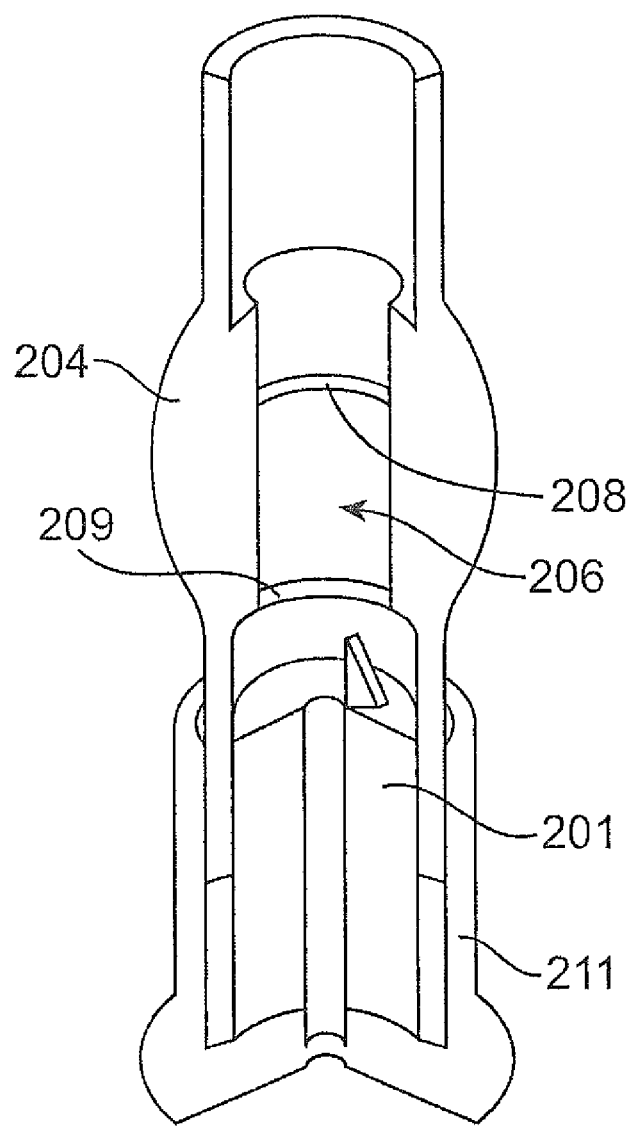
FIG. 3B is a cutaway view of the second portion, plunger and cap of FIG. 3A prior to use.
Figure 3C:
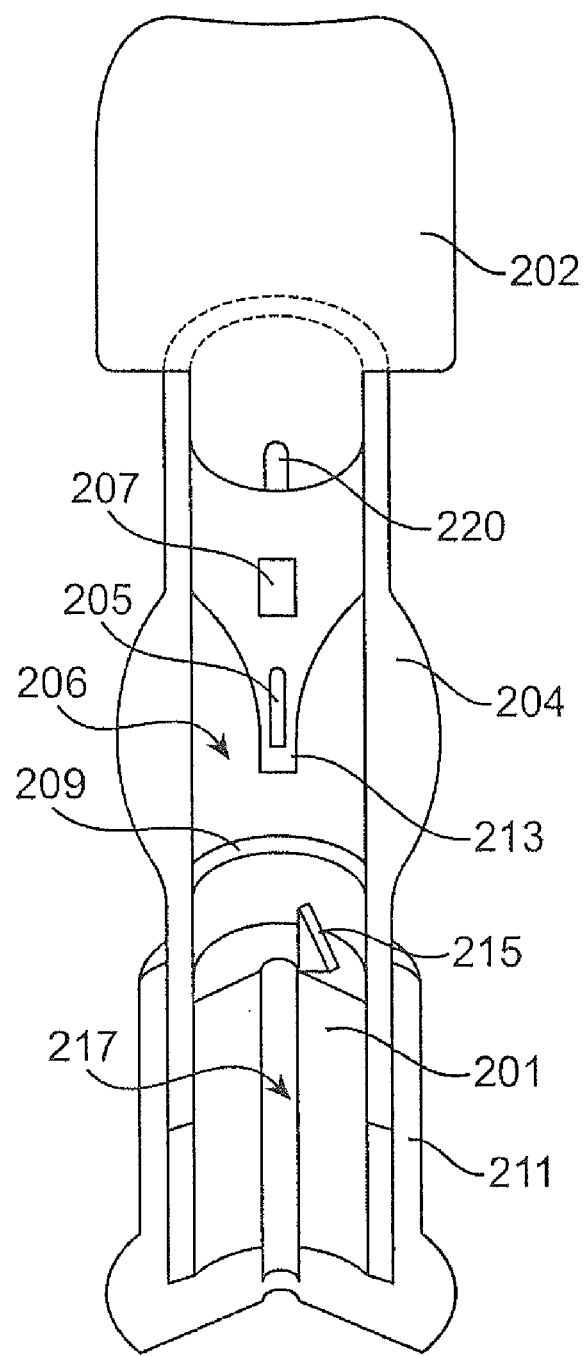
FIG. 3C is a cutaway view similar to FIG. 3B, but with the first portion of the device fully inserted into the second portion of the device.
Figure 3D:
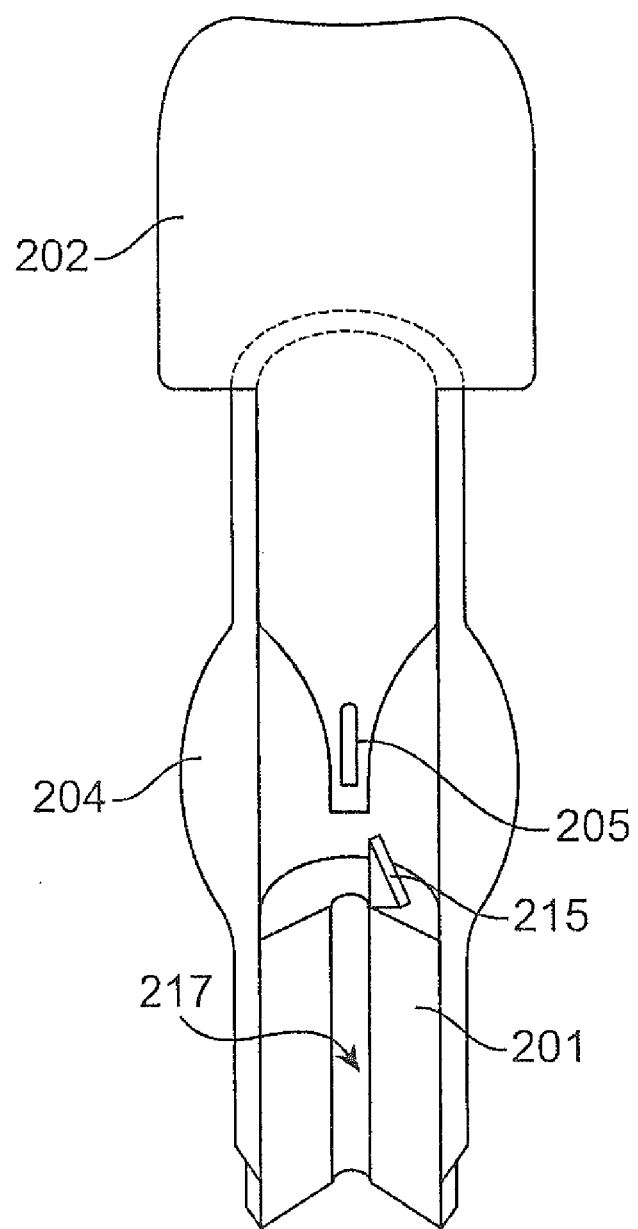
FIG. 3D is a cutaway view similar to FIG. 3C, but with the cap removed and plunger fully inserted into the second portion of the device.

As seen in FIG. 3B, plunger 201 initially sits in the bottom of second portion 204. Both plunger 201 and second portion 204 sit within cap 211. Next, as seen in FIG. 3C, first portion 202 is inserted into second portion 204 (as described above). At this time, septum piercing projection 203 will rupture (top) septum 208 such that the contents of capillary channel 205 and sample treatment chamber 206 can be mixed. Next, as seen in FIG. 3D, cap 211 is removed, and plunger 201 is pushed upwardly into second portion 204. At this time, a spike 215 on plunger 201 will rupture (bottom) septum 209 such that the mixed contents of sample treatment chamber 206 can be ejected from the bottom of device 200. For example, through plunger 201 (similar to the approach seen in FIG. 1F).

In one optional aspect of the invention, plunger 201 includes a central flow channel 217. The sharp top end of spike 215 can be positioned adjacent to central flow channel 217. In one optional embodiment, the sharp end of spike 215 can be positioned slightly over the top of central flow channel 217.

It is to be understood that the present invention is not limited to use with blood samples. Instead, any other fluid that is to be analyzed in any type of fluid analysis meter may be substituted. As such, the present invention encompasses operation with various fluid samples, including body fluid samples that include analytes such as prostate specific antigen, lipids, creatinine, microalbumin, etc.

Preferably, the meter with which device 200 is used is a HbAlc meter, however, it is to be understood that the present invention is not so limited. Instead, any form of analyte meter (for measuring one or more analytes) is compatible with the present invention. Thus, the present invention may entail, but is not limited to, mixing a blood sample with a dilution buffer. For example, the present invention may also be useful for mixing blood with other substances, and may also be used in conjunction with other devices. The functioning of an exemplary meter was described in U.S. Pat. Nos. 5,837,546; 5,945,345 and 5,580,794, incorporated by reference herein in their entirety. It is to be understood, however, that the present the invention may also be used with any suitable fluid analysis meter, or even with a simple containment vessel (e.g.: for preparing a sample for deposition in a well, such that it can be analyzed in future).

In optional aspects of the invention, device 200 may be used with either: a single use test meter (as was described in U.S. Pat. Nos. 5,837,546; 5,945,345 and 5,580,794), or a multi-use cartridge system as described in U.S. Provisional Application No. 60/550,410.

What is claimed:

1. A device for preparing a fluid sample for use in a fluid analyte meter, comprising:
   a first portion, comprising:
   a septum piercing projection,
   a capillary channel, and
   a vent on an outer surface of the first portion; and
   a second portion, comprising:
   a treatment solution chamber, and
   a septum sealing the treatment solution chamber, wherein the vent is open when the first portion of the device is initially inserted into the second portion of the device, and wherein the vent is closed when the first portion of the device is fully inserted into the second portion of the device.

2. The device of claim 1, wherein the vent permits air to escape from within the second portion of the device as the first portion of the device is inserted into the second portion of the device.

3. The device of claim 1, wherein the vent comprises a slot extending along a portion of the outer surface of the first portion of the device.

4. The device of claim 3, wherein the slot extends from a leading edge of the outer surface part way along the length of the outer surface of the first portion of the device.

5. The device of claim 3, wherein the outer surface of the first portion of the device is positioned against an inner surface of the second portion of the device when the first portion of the device is fully inserted into the second portion of the device.

6. A device for preparing a fluid sample for use in a fluid analyte meter, comprising:
   a first portion having a capillary channel dimensioned to receive a fluid sample therein, and having a vent on an outer surface;
   a second portion having a treatment solution chamber enclosed by first and second septums, wherein the first portion penetrates the first septum when the first portion is inserted into the second portion such that contents of the treatment solution chamber mix with contents of the capillary channel, wherein the vent is open when the first portion of the device is initially inserted into the second portion of the device, and wherein the vent is closed when the first portion of the device is fully inserted into the second portion of the device; and
   a mechanism for penetrating the second septum such that contents of the treatment solution chamber and the capillary channel can be ejected from the device.

7. The device of claim 6, wherein the vent permits air to escape from within the second portion of the device as the first portion of the device is inserted into the second portion of the device.

8. The device of claim 6, wherein the vent comprises a slot extending along a portion of the outer surface of the first portion of the device.

9. The device of claim 7, wherein the slot extends from a leading edge of the outer surface part way along the length of the outer surface of the first portion of the device.

10. The device of claim 7, wherein the outer surface of the first portion of the device is positioned against an inner surface of the second portion of the device when the first portion of the device is fully inserted into the second portion of the device.

11. A device for preparing a fluid sample for use in a fluid analyte meter, comprising:
   a first portion having a capillary channel dimensioned to receive a fluid sample therein;
   a second portion having a treatment solution chamber enclosed by first and second septums, wherein the first portion penetrates the first septum when the first portion is inserted into the second portion such that contents of the treatment solution chamber mix with contents of the capillary channel; and a plunger having a mechanism for penetrating the second septum such that the contents of the treatment solution chamber and the capillary channel are ejected through the plunger.

12. The device of claim 11, wherein the mechanism for penetrating the second septum comprises a spike on the plunger.

13. The device of claim 12, wherein the plunger comprises a central flow channel, and wherein the spike is positioned adjacent to the central flow channel.

14. The device of claim 13, wherein a sharp end of the spike is positioned over the central flow channel.

* * * * *